US00PP10683P

United States Patent [19]

De La Torre

[11] Patent Number: Plant 10,683

[45] Date of Patent: Nov. 10, 1998

[54] GAZANIA PLANT NAMED 'ARMSTRONG'S GOLD'

[75] Inventor: Jose Jaime De La Torre, Ontario, Calif.

[73] Assignee: DLT Growers, Ontario, Calif.

[21] Appl. No.: 910,473

[22] Filed: Jul. 25, 1997

[51] Int. Cl.[6] ..... A01H 5/00

[52] U.S. Cl. ..... Plt./87.14

[58] Field of Search ..... Plt./87.14

*Primary Examiner*—Howard J. Locker

*Attorney, Agent, or Firm*—C. A. Whealy

[57] ABSTRACT

A distinct cultivar of Gazania plant named Armstrong's Gold, characterized by its large and numerous golden yellow inflorescences; vigorous, rapid growth rate, and early flowering; reduced susceptibility to fungal pathogens common to Gazanias; and excellent garden ground cover performance.

1 Drawing Sheet

The present invention relates to a new and distinct cultivar of Gazania plant, botanically known as *Gazania rigens* and referred to by the cultivar name Armstrong's Gold.

The new cultivar was selected by the inventor in June, 1995, from seedling progeny from a cross of unidentified selections of *Gazania rigens* in an outdoor production area in Ontario, Calif.

Asexual reproduction of the new cultivar by terminal crown cuttings taken at Ontario, Calif., has shown that the unique features of this new Gazania are stable and reproduced true to type in successive generations.

The following traits have been repeatedly observed and are determined to be the unique characteristics of Armstrong's Gold. These characteristics in combination distinguish Armstrong's Gold as a new and distinct cultivar:

1. Large and numerous golden yellow inflorescences.
2. Vigorous, rapid growth rate, and early flowering.
3. Less susceptible to fungal pathogens common to Gazanias.
4. Excellent garden ground cover performance.

The new cultivar can be compared to the *Gazania rigens* cultivar Mitsuwa Yellow (not patented). However in side-by-side comparisons conducted in Ontario, Calif., plants of the new cultivar differ from plants of the cultivar Mitsuwa Yellow in the following characteristics:

1. Plants of the new cultivar are more vigorous, grow faster, and flower earlier than plants of the cultivar Mitsuwa Yellow.
2. Plants of the new cultivar have longer internodes than plants of the cultivar Mitsuwa Yellow.
3. Plants of the new cultivar have 50 percent more inflorescences than plants of the cultivar Mitsuwa Yellow.
4. Plants of the new cultivar have inflorescences that are 30 percent larger than plants of the cultivar Mitsuwa Yellow.
5. Plants of the new cultivar have inflorescences that have six to eight more ray florets than plants of the cultivar Mitsuwa Yellow.
6. Ray floret color of plants of the new cultivar is slightly darker than the ray floret color of plants of the cultivar Mitsuwa Yellow.
7. Plants of the new cultivar have narrower leaves than plants of the cultivar Mitsuwa Yellow.
8. Plants of the new cultivar are less susceptible to fungal pathogens common to Gazanias than plants of the cultivar Mitsuwa Yellow.

The cultivar Armstrong's Gold has not been observed under all possible environmental conditions. The phenotype may vary somewhat with variations in environment such as temperature, daylength and light intensity, without, however, any variance in genotype.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of the new Gazania. Floret and foliage colors in these photographs may vary from the actual floret and foliage colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in an outdoor production area in Ontario, Calif. Day temperatures ranged from 27° to 32° C. and night temperatures were usually about 10° C.

Botanical classification: *Gazania rigens* cultivar Armstrong's Gold.

Parentage:

Seedling of unidentified *Gazania rigens* selections.

Propagation:

*Type*.—Vegetative crown terminal cuttings.

*Time to rooting*.—Summer: About 10 days at 27° to 32° C. Winter: About 14 days at 18° to 21° C.

*Rooting habit*.—Fine and well-branched.

Plant description:

*Appearance*.—Perennial herbaceous decorative ground cover. Plants horizontal and outwardly spreading.

*Vigor*.—Vigorous and rapid growth rate. Usually only four weeks are required to produce a flowering flat container of the new cultivar.

*Plant height*.—20 to 25 cm.

*Plant width*.—90 to 120 cm. *Lateral branch description*.—Internode length: About 5.6 cm. Texture: Glabrous to puberulent. Color: 145C.

*Foliage description*.—Arrangement: Alternate, single. Length: About 9.4 cm. Width: About 10.7 mm. Shape: Oblanceolate. Apex: Acute. Base: Attenuate. Margin: Crenulate to serrulate. Texture: Upper surface: Glabrous. Under surface: Tomentose. Petiole: Length: About 2.6 cm. Diameter: About 3 mm. Color: Young foliage upper surface: 137A. Young foliage under surface; 190D. Fully expanded foliage upper surface: 137A. Fully expanded foliage under surface: 190D. Venation, upper surface: 138B. Venation, under surface: 139D. Petiole: 145B.

Flowering description:

*Appearance*.—Daisy inflorescence form. Inflorescences borne on terminals above foliage, arising from leaf axils. Disc and ray florets arranged acropetally on a capitulum. Usually one inflorescence per terminal, inflorescences upright and not persistent.

*Flowering response*.—Under natural conditions, plant flowers from the spring until the fall.

*Inflorescence longevity*.—On plant: 5 to 10 days. As a cut flower: 3 to 6 days.

*Inflorescence size*.—Diameter: 3.9 to 4.3 cm. Depth (height): 1.7 to 2 cm. Diameter of disc: 1.5 to 2 cm. Capitulum diameter: 1 to 1.2 cm. Capitulum depth (height): 1.6 to 1.9 cm.

*Ray florets*.—Quantity per inflorescence: 13 to 16. Shape: Oblanceolate to obovate. Length: 2.6 to 2.9 cm. Width: 7 to 9 mm. Apex: Obtuse. Base: Acuminate. Margin: Entire. Texture: Velvety and smooth. Aspect: Flat. Color: When opening, upper surface: 14A. When opening, under surface: 13B. Mature, upper surface: 14A. Mature, under surface: 14B. Fading to: 14B.

*Disc florets*.—Quantity per inflorescence: 85 to 110. Shape: Cylindrical. Length: 7 to 8 mm. Width: 1.5 to 2 mm. Color, immature and mature: 17B.

*Peduncle*.—Aspect: Erect. Length: 9 to 11 cm. Color: 152C.

*Sepals*.—Appearance: Paleaceous. Quantity per inflorescence: 1 to 4. Shape: Linear. Apex: Acute. Margin: Entire to fimbriate. Texture: Fine white pubescence.

*Inflorescence bud*.—Length: 7 to 12 mm. Diameter: 5 to 8 mm. Shape: Ovoid. Color: 144B.

*Reproductive organs*.—Androecium: Stamen number: Five. Anther shape: Linear. Anther size: About 2 mm. Anther color: 20A. Pollen: Moderate. Pollen color: 20A. Gynoecium: Pistil length: 8 to 10 mm. Stigma shape: Bifid. Stigma color: 9C. Style length: 7 to 9 mm. Style color: 1D. Ovary color: 155D.

Disease resistance: Less susceptible to fungal pathogens common to Gazania plants.

Seed production:

*Length*.—About 3 mm.

*Diameter*.—About 1 mm.

*Color*.—177A.

It is claimed:

1. A new and distinct cultivar of Gazania plant named Armstrong's Gold, as illustrated and described.

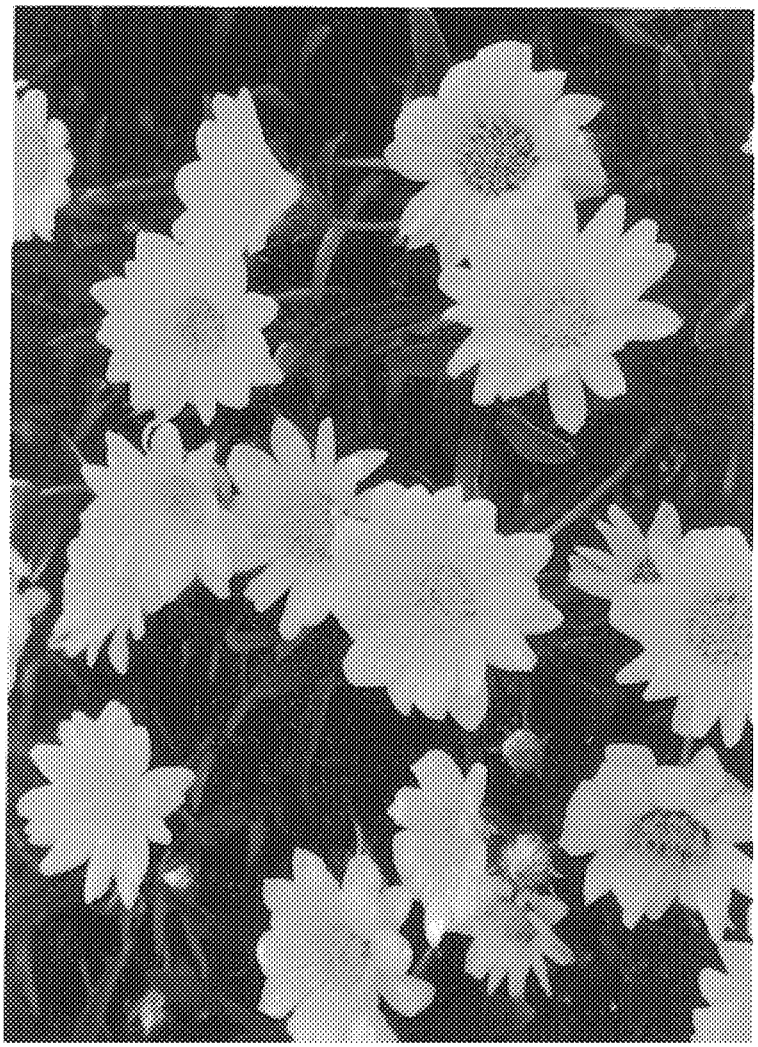

* * * * *